US00PP10538P

United States Patent [19]

Danziger

[11] Patent Number: Plant 10,538

[45] Date of Patent: Aug. 4, 1998

[54] NEW GUINEA IMPATIENS PLANT NAMED 'DANITARA'

[75] Inventor: Gaby Danziger, Nir Zvi, Israel

[73] Assignee: Danziger "Dan" Flower Farm, Post Beit Dagan, Israel

[21] Appl. No.: 677,853

[22] Filed: Jul. 10, 1996

[51] Int. Cl.[6] ..... A01H 5/00

[52] U.S. Cl. ..... Plt./87.6

[58] Field of Search ..... Plt./87.6

[56] References Cited

U.S. PATENT DOCUMENTS

P.P. 6,925 7/1989 Kientzler ..... Plt./87.6
P.P. 9,991 8/1997 Kientzler ..... Plt./87.6

*Primary Examiner*—Howard J. Locker
*Assistant Examiner*—Kent L. Bell
*Attorney, Agent, or Firm*—Foley & Lardner

[57] ABSTRACT

A new and distinct cultivar of Impatiens plant named 'Danitara', characterized by the combined features of bright red-purple flower color, solid dark green leaves, compact growth habit, and long pedicels which carry the flowers evenly well above the foliage.

1 Drawing Sheet

The present invention relates to a new and distinctive cultivar of Impatiens plant, botanically known as Impatiens, commercially known as New Guinea Impatiens, and known by the cultivar name 'Danitara'.

Danitara was developed by the inventor Gaby Danziger in a controlled breeding program in Mishmar Hashiva, Israel by crossing the cultivar identified as '7-11' (seed parent), with the cultivar identified as '3-75' (pollen parent). Both cultivars are proprietary.

Asexual reproduction of the new cultivar by leaf cuttings taken by the inventor at Mishmar Hashiva, Israel has shown that the unique features of this new Impatiens plant are stabilized and are reproduced true to type in successive propagations.

The following characteristics distinguish the new impatiens from both its parent varieties and other cultivated impatiens of this type known and used in the floriculture industry:

1. Bright red-purple flower color.
2. Solid dark green leaves.
3. Compact growth habit.
4. The flowers are carried on relatively long pedicels and are spread evenly above the foliage.

In the accompanying colored photographic drawings, the photograph at the top of the sheet comprises a top view showing the overall appearance of a typical plant or the new cultivar, with the close-up photograph at the bottom of the sheet showing flowers and foliage in much greater detail. The true flower color is not accurately shown in the top photograph, but is depicted fairly closely in the close-up photograph. It is anticipated that this plant will be marketed under the trademark "Tarantella".

Danitara is particularly distinguished by its large purple-pink flowers and solid dark green leaves, and those combined characteristics are unique. When compared to the cultivar Mimas, disclosed in U.S. Plant Pat. No. 6,925, Danitara is more compact, its flowers are larger, and it flowers earlier than Mimas when the cultivars are grown under similar conditions.

The following is a detailed description of my new Impatiens cultivar based on plants produced under commercial practice in Mishmar Hashiva, Israel. The plants were grown in a net-covered greenhouse during spring time, with a maximum temperature of 30° C. and a minimum temperature of 18° C.

Color references are made to The Royal Horticultural Society Colour chart except where general terms of ordinary dictionary significance are used.

Parentage: Seedling from '7-11×3-75'.

Propagation:

*Type cutting.*—Leaf cuttings.

*Time to initiate roots.*—7–8 days at 25° C. in summer and 8–9 days at 20° C. in winter, about 20–25 roots per plant, each approximately 2–3 cm in length and 0.5–1.0 mm thick.

*Rooting habit.*—Roots well.

Plant description:

*Form.*—As measured 4 months after planting a single young plant in a 16 cm pot, the plant was approximately 26–40 cm in height and 21–50 cm in width.

*Habit.*—Compact.

*Foliage (mature).*—Size: Approximately 80 mm long and 30–35 mm wide. Shape: Oblong, leaf apex is acuminate and base is rounded; texture is typical for the species. Margin: Serrated. Color: Young foliage, top side 139A, under side 138A; mature foliage, top side 138A, under side 139A. Venation: Pinnate; the main vein is partially red, approximately one-third of the length thereof closest to the base; secondary veins are green, vein color underside is somewhat lighter.

Flowering description:

*Flowering habits.*—Flowers develop well above the foliage, and cover the entire plant.

*Natural flowering season.*—Flowering is year around in temperatures between 5C and 25C; not tolerant to frost.

*Flower buds.*—There are 3–6 buds on each axil, with each bud before opening being oval shape and 1.0–1.5 cm in length along its major axis. Buds are carried on long light red pedicels 55 mm in length, with purple spurs (R.H.S. 61B). Spur is half-rounded in shape and 3.1–5.0 cm in length.

*Flower borne.*—The flowers are carried on pedicels that terminate well above the foliage, with the flowers being spread evenly. Flowering commences 45–50 days after planting under normal growing conditions.

*Quantity of flowers.*—Medium.

*Petals.*—Shape: Typical, two heart-shaped pairs of petals, with each petal being approximately 2.2–2.6 cm in width and 2.2–2.7 cm in length; the remaining petals is relatively larger at 3.0–3.5 cm in width and 2.0 cm in length. Color: Top side when opening 74A, with no fading; under side 67B. Number of petals: 5. Size of flowers: Medium, approximately 4.8 cm in diameter.

*Reproductive organs.*—Stamens: One (1) in number. Anther shape: Round, color red 42A. Pollen color: White. Pistils: Stigma shape: Round, color nearly white. Style color: Green. Ovaries: Four, 1 mm in size, green in color.

*Disease resistance.*—no abnormal disease problems have been noted to date.

I claim:

1. A new and distinct cultivar of Impatiens plant named 'Danitara', as illustrated and described.

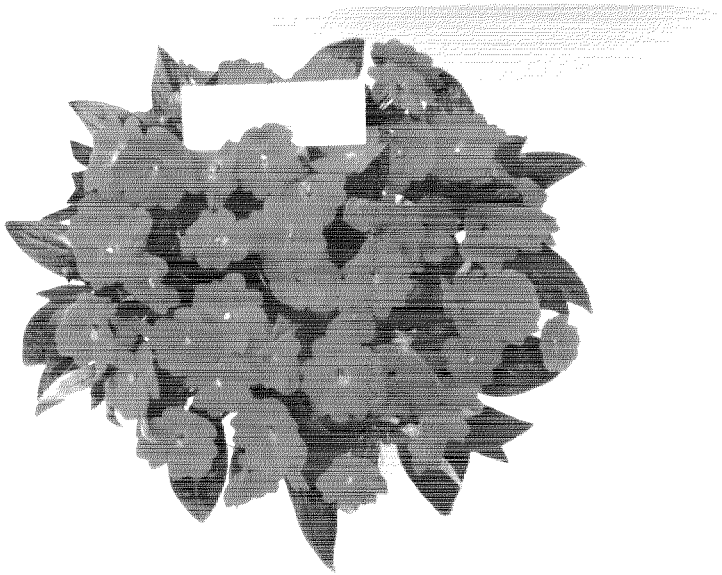
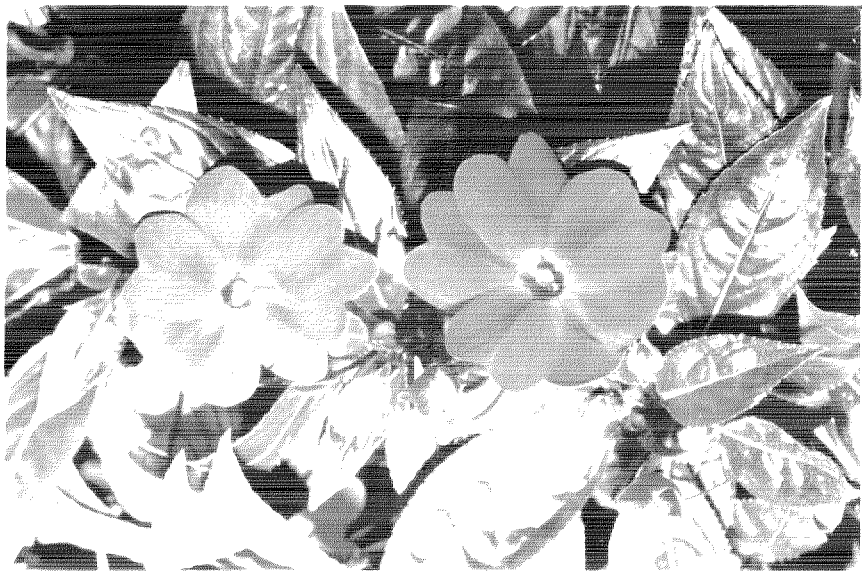

* * * * *